United States Patent [19]

Wedding

[11] Patent Number: 4,461,183
[45] Date of Patent: Jul. 24, 1984

[54] AMBIENT AEROSOL SAMPLER INLET

[76] Inventor: James B. Wedding, 2128 Sandstone Dr., Fort Collins, Colo. 80524

[21] Appl. No.: 354,940

[22] Filed: Mar. 5, 1982

[51] Int. Cl.$^3$ .................. G01N 1/02; B01D 45/12
[52] U.S. Cl. .................... 73/863.21; 55/270; 55/337; 55/392; 55/449
[58] Field of Search ............... 73/863.21, 863.22, 28; 55/337, 449, 392, 270, 318, 325, 447, DIG. 14, 448, 450; 209/144, 211

[56] References Cited

U.S. PATENT DOCUMENTS

| | | | |
|---|---|---|---|
| 1,518,152 | 12/1924 | Kingdon | 55/270 |
| 2,626,013 | 1/1953 | Reimann | 55/327 |
| 3,521,431 | 7/1970 | Connors et al. | 55/318 |
| 4,255,172 | 3/1981 | Smith | 73/28 |

FOREIGN PATENT DOCUMENTS

| | | | |
|---|---|---|---|
| 55-109420 | 8/1980 | Japan | 55/270 |
| 241602 | 10/1925 | United Kingdom | 55/DIG. 14 |
| 257168 | 8/1926 | United Kingdom | 55/449 |

Primary Examiner—Gerald Goldberg
Assistant Examiner—John E. Chapman, Jr.

[57] ABSTRACT

An ambient aerosol sampling device according to the disclosure herein includes a cyclonic fractionator comprised of an inner tube positioned partially inside a larger diameter middle tube that is plugged at the bottom. A still larger sized outer tube is positioned over the middle tube to receive air flow out of the middle tube and direct it to a conventional filter substrate. A plurality of vanes are positioned at the inlet of the inner tube to impart a vertical motion to an air stream flowing therein. A protective cover is positioned over the vanes and cyclonic fractionator, and an aerodynamic deflector at the bottom of the cover and air ramp inside the cover provides an omni-directional inlet pathway to draw air into the sampling device and to guide the airstream into the vanes.

18 Claims, 6 Drawing Figures

AMBIENT AEROSOL SAMPLER INLET

BACKGROUND OF THE INVENTION

The present invention is related generally to aerosol sampling devices, and specifically to an aerosol sampler inlet in the form of a cyclone fractionator adapted for accurate, omni-directional air sampling of particulate substances in the air.

It is recognized and generally accepted that chemical air pollution is deleterious to the health of persons. Scientists are becoming aware that particulate pollution in air also has adverse effects on the health of persons. The U.S. Environmental Protection Agency has set present standards for particulate matter in air in terms of mass per unit volume limits over a preselected period of time. For example, present standards for particulate matter are 75 micrograms per cubic meter average annular limit (geometric mean) and 260 micrograms per cubic meter in 24 hours (geometric mean) for particles larger than 45 microns.

New data have recently become available which indicate that protection of public health may be served better by considering only inhalable particles. The International Standards Organization has proposed a standard based upon particles deposited on the tracheobronchial and alveolar regions of the human respiratory tract. This proposal is now referred to as thoracic deposition or TPC (Thoracic Particles). The Clear Air Scientific Advisory Committee (CASAC) has now recommended to the United States Environmental Protection Agency that a 10 micron particle size range be used as the new primary standard for average annual limits and 24 hour limits of micrograms per cubic meter clean air standards. Therefore, a need exists to develop monitoring instruments that mimic the deposition of particles in the thoracic region of the human respiratory system.

An ideal inlet for assessing the true ambient particulate concentration is defined by a log-normal effectiveness curve having a $D_{50}$ equal to 10 microns and a unity slope, where $D_{50}$ is defined as the particle size associated with a sampling effectiveness of 50 percent. This ideal inlet is that which has the performance specification of sampling 100% of the available ambient airborne particulate mass. Effectiveness is defined as the ratio of mass deposited on the collection substrate of the sampler to the total airborne mass approaching the inlet and with the proper corrections made for sampling volumes. Such an ideal inlet could also be defined as one in which performance characteristics allow collection of an accurate mass representative sample of the TP fraction independent of the sampling conditions of wind speed and direction. Prior to this invention, no such sampling devices were available.

SUMMARY OF THE INVENTION

Accordingly, it is an object of the present invention to provide a novel ambient aerosol sampler inlet whose performance is described by a collection effectiveness aerodynamic diameter curve having the same $D_{50}$, slope, and shape independent of the sampling conditions which delineates the capability of said sampler of collecting all particles of interest.

It is also an object of the present invention to provide an ambient aerosol sampler having an aerosol sampler inlet capable of obtaining the desired particle effectiveness required by proposed changes in the ambient aerosol sampler standards set by governmental regulations or other criteria, e.g., 10 microns based upon best attempts to mimic deposition in a thoracic region of the human respiratory tract.

Another object of the present invention is to provide an ambient aerosol sampler inlet having a suitable inlet housing and aerodynamic pathway which is capable of transporting to the fractionator and subsequently to the filter substrate representative sample of particle laden air under all reasonable ambient conditions and specifically independent of ambient wind direction and velocity over the range of 2 to 24 Km/hr.

Still another object of the present invention is to provide an ambient aerosol sampler having an inlet geometry capable of transporting the aerosol effeciently and without loss or deposition of particles to the fractionator while protecting the system from environmental factors.

It is also an object of the present invention to provide an ambient aerosol sampler device having a suitable particle fractionator that is not susceptible to particle bounce or other factors that could cause enrichment or otherwise inaccurate sampling results.

A still further object of the present invention is to provide an ambient aerosol sampler inlet with a fractionating device in which particles are not collected or deposited in areas or on components of the apparatus in a manner that would alter the performance of the inlet over a long period of time.

It is also an object of the present invention to provide an ambient aerosol sampler that is accurate, convenient, and does not require unpredictable maintenance.

The ambient aerosol sampler inlet device of the present invention designed with these objects in mind includes a cyclone type particle fractionator for separating solid particles from a moving air stream, an omnidirectional inlet airflow path for directing aerosol from any direction into the fractionator, and an airflow exhaust or outlet where the flow of air is drawn off or out of the fractionator. It also includes air directing apparatus at the fractionator inlet for imparting a vortical motion to the airflow. The air directing apparatus includes a plurality of vanes positioned in angularly spaced apart relation to each other around the inlet of the cyclone particle fractionator. Each of the vanes has a two dimensional airfoil-shaped longitudinal cross-section and is oriented to extend tangentially outward from the inlet of the cyclone particle fractionator.

The cyclone particle fractionator includes an elongated inner tube positioned concentrically inside a larger diameter elongated middle tube. The bottom of the middle tube is plugged so that air flows downwardly through the inner tube in a vortical motion and then upwardly through the annulus between the inner tube and the middle tube. A still larger diameter outer tube is positioned over the middle tube and plugged at the top so that airflow exiting the middle tube continues its flow downwardly through the annulus between the outer tube and the middle tube. The outer tube is adapted to be connected to a conventional filter substrate and vacuum pump for drawing the air through the ambient aersol sampler device and collecting the remaining particles in the aerosol that are not cut in the fractionator, i.e., particles less than 10 microns in size. Neither the vacuum source nor the substrate filter are a part of this invention.

A generally cylindrical cover is positioned concentrically around the outer tube and is open at the bottom but closed at the top for directing inlet air into the air directing vane structure at the top of the fractionator. An aerodynamic flow ramp is also positioned inside the cover and extends downwardly and outwardly from the open bottom of the cover to form an omni-directional aerosol intake for diverting ambient airflow into the ambient aerosol sampler.

DESCRIPTION OF THE DRAWINGS

Other objects, advantages, and capabilities of the present invention will become apparent as the description proceeds taken in conjunction with the accompanying drawings, in which.

DETAILED DESCRIPTION OF THE PREFERRED EMBODIMENTS

Figure 1:
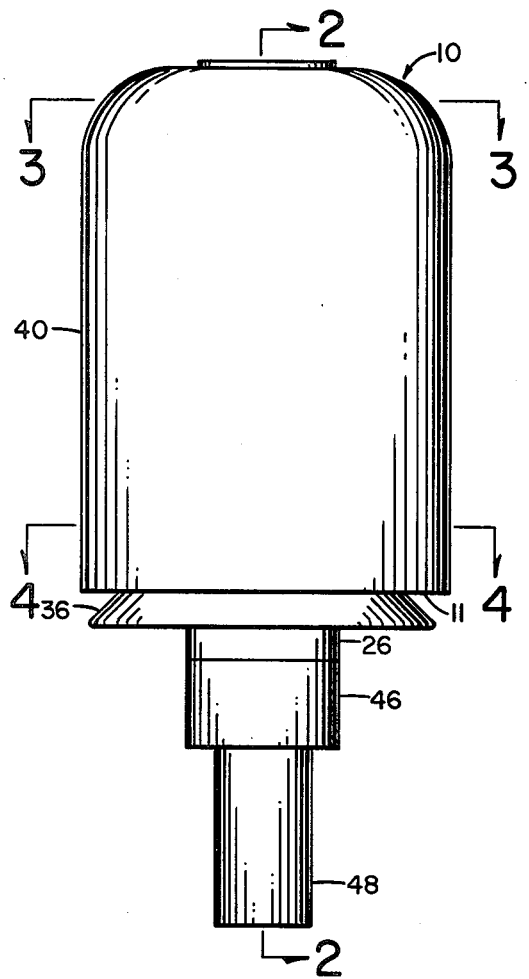
FIG. 1 is an elevation view of the ambient aersol sampler inlet device of the present invention.

The ambient aerosol sampler inlet device 10 of the present invention, as shown in FIGS. 1 through 4, is comprised primarily of a cyclone fractionator 12, an assembly of airflow directing vanes 30 positioned around the inlet of the particle fractionator 12, a cylindrical cover 40 positioned over the fractionator 12 and vane assembly 30, and an aerodynamic flow deflector or ramp 36 positioned inside the cover 40 to form an efficient airflow path to direct a stream of air into the vane structure 30.

The particle fractionator 12 is comprised primarily of a vertical elongated cylindrical first or inner tube 14 with a larger diameter elongated cylindrical second or middle tube 18 positioned concentrically around the lower portion of the inner tube 14. Preferably, a substantial portion of the middle tube 18 extends downwardly below the bottom end 16 of the inner tube 14, and the upper end 15 of the inner tube 14 extends upwardly beyond the upper end 19 of the middle tube 18. A plug 21 is positioned in the lower end 20 of middle tube 18, while the upper end 19 of middle tube 18 is left open.

A third or outer tube 24 having a larger diameter and being longer then middle tube 18 is positioned concentrically over middle tube 18. Preferably, the upper end 25 of outer tube 24 extends upwardly beyond the upper end 19 of middle tube 18, and the lower end 26 of outer tube 24 extends downwardly below the lower end 20 of middle tube 18. A suitable coupling, such as the tapered coupling 46 shown in FIG. 2, is provided to connect a tube 48 from a vaccum source and filter substrate (not shown) to the outer tube 24.

Figure 4:
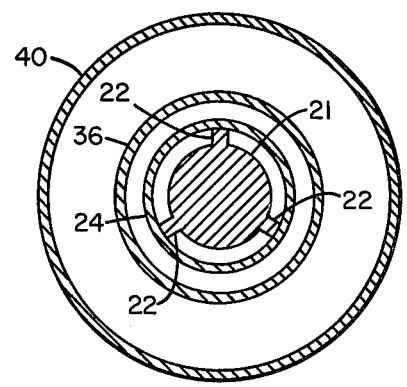
FIG. 4 is a cross-sectional view of the ambient aerosol sampler inlet device of the present invention taken along lines 4—4 of FIG. 1.
Figure 5:
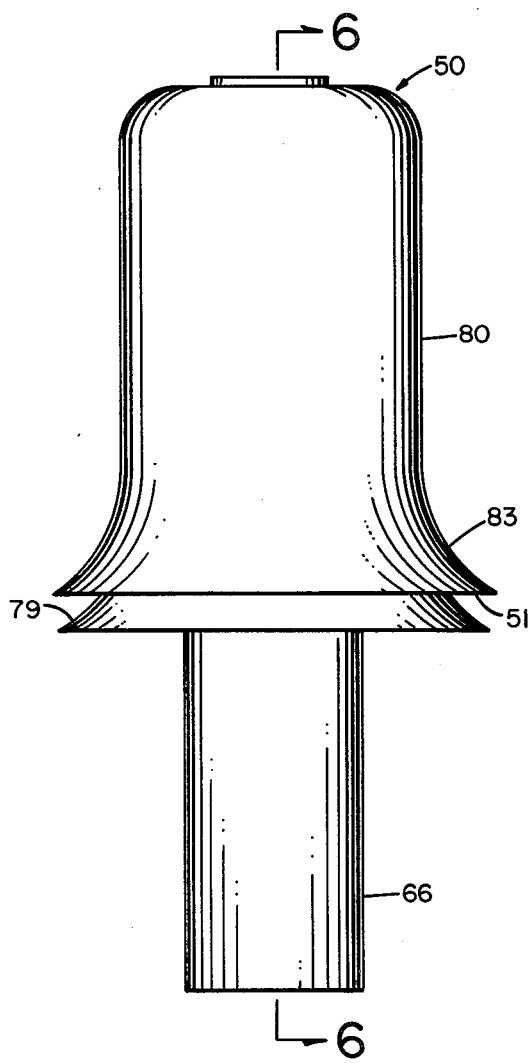
FIG. 5 is an elevation view of an alternate embodiment ambient aerosol sampler inlet device according to the present invention.

A circular vane assembly base 28 is positioned over the upper end 25 of outer tube 24 to plug the upper end 25 of the tube 24 and to provide a base on which a plurality of air directing vanes 30 are positioned around the inlet end of inner tube 14. The upper end 15 of inner tube 14 extends upwardly into a central bore 29 in the vane assembly base 28 in such a manner that the vane assembly base 28 provides a unitary structure support for the inner tube 14, outer tube 24, and vanes 30. As best seen in FIG. 4, the plug 21 in the lower end 20 of middle tube 18 includes a plurality of legs or spacers 22 extending radially outwardly therefrom into contact with the interior of the outer tube 24 to provide support for the middle tube 18.

Figure 2:
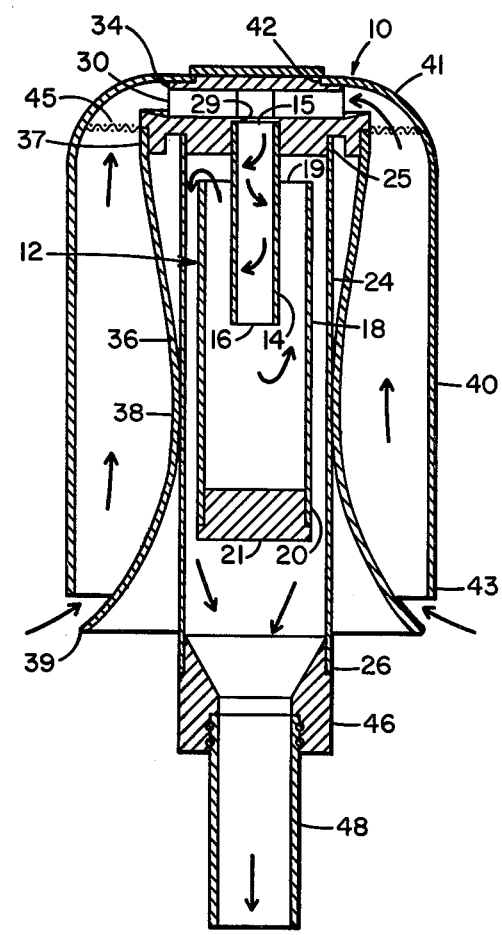
FIG. 2 is a cross-sectional view of the ambient aerosol sampler inlet device of the present invention taken along lines 2—2 of FIG. 1.
Figure 3:
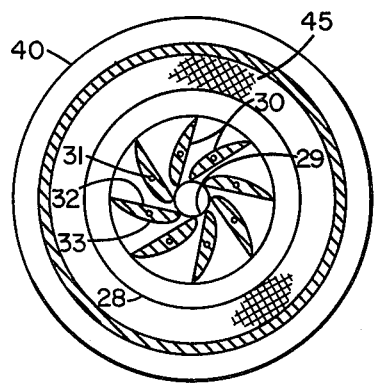
FIG. 3 is a cross-sectional view of the ambient aerosol sampler inlet device of the present invention taken along 3—3 of FIG. 1.

As best seen in FIGS. 2 and 3, the vane assembly is comprised of a plurality of vanes 30 positioned on the vane assembly base 28 around the inlet or upper end 15 of inner tube 14. Each vane 30 has a two dimensional cross-section in a plane perpendicular to the longitudinal axis of said inner tube 14. One side 32 of the vane 30 in the cross-section is straight, and the opposite side 33 of the vane 30 in cross-section is a curved shape similar to an airfoil in appearance, although not in function. In other words, the side 33 diverges outwardly in a smooth curve away from an intersection with the straight side 32 at the proximal end of the vane 30 adjacent the inlet of inner tube 14 and then converges back toward the straight side 32 to intersect again at the distal end of the vane 30 a spaced distance outwardly from the inlet of inner tube 14. The convergence of the curved side 33 is less severe, or at a smaller angle, than the divergence so that its appearance is similar to an airfoil or the cross-section of an airplane wing. As shown in FIG. 3, eight of such vanes 30 are positioned in angularly spaced apart relation to each other around the bore 29 in vane assembly base 28. The straight side 32 on each vane 30 extends tangentially outward from the bore 29 with the enlarged portion of the curved side 33 nearer to the proximal end adjacent bore 29 than to the distal end. In other words, each vane is positioned with its flat side or straight side 32 at an angle in the radius of the bore 29 in a position to impart vortical motion to an airstream entering inner tube 14. A top plate 34 is positioned over the vanes 30, and a retainer pin 31 extends through each vane 30 and into the vane assembly base 28 to retain the vanes 30 in proper position. This two dimensional design of the vanes 30 is effective to minimize or eliminate any particle deposition or build up in the vanes 30 which could adversely affect the performance of the sampler or the accuracy of the sample obtained over a period of time.

The aerodynamic flow deflector or ramp 36 is a somewhat hourglass-shaped figure of revolution tapered downwardly from its upper end 37 toward its mid-section 38 and is flared outwardly in a concave cross-section from its mid-section 38 toward the lower end 39. The top edge 37 of the air ramp 36 is attached to and supported by the peripheral surface of the vane assembly base 28.

The cylindrical cover 40 is positioned concentrically around the air ramp 36. The bottom of the cover is open, and the lower rim 43 thereof is positioned a spaced distance upwardly from the lower rim 39 of the air ramp 36. The upper end 41 of the cover 40 is curved inwardly toward its longitudinal axis to close onto the vane assembly top plate 34.

The lowered flared portion 39 of ramp 36 provides an omni-directional aerodynamic flow deflector to defect ambient air into the inlet device 10. The space between the lower rim 43 of cover 40 and the flared rim 39 of air ramp 36 forms an aerodynamic pathway 11 to direct the airstream upwardly into the vanes 30. The contoured air ramp 36 is effective to direct the airflow efficiently without turbulence or particle deposition to the vanes 30. The bug screen 45 positioned across the aerodynamic inlet flow path near the top of the ramp 36 is effective to prevent flying insects or large debris from entering the vanes 30 or fractionator 12.

As mentioned above, a vacuum pump is connected to a tube 48, and a conventional filter (not shown) is provided upstream from the vacuum pump to filter out and catch all the particulate matter than is not fractionated out of the airstream by the fractionator 12. Since the vacuum pump and filter assembly for collecting these particles is conventional and well known to those skilled in the art, it is not necessary to illustrate them here.

In operation, a conventional filter substrate and vacuum pump (not shown) are connected to tube 48 to draw air through the inlet structure 10 and to deposit and retain particles not removed in the fractionator for analysis. The omni-directional aerodynamic deflector 39 and inlet pathway 11 at the bottom of the cover 40 allow aerosol entry from any angle of approach, regardless of the wind direction or velocity. The airstream is directed upwardly along the ramp 36 to the upper end of the cylindrical cover 40 where it is turned horizontally into the vane structure 30. An angular impetus is imparted to the particle laden airstream by the evenly spaced entrance vanes 30 so that the downward flow of air and particles through the interior of inner tube 14 is in a vortical motion. Particle removal is realized on the surface of the inner collection tube 14. In keeping with the proposed inhalable particle or TP standards, the particle size cut point in this cyclone fractionator is 10 microns. These results are obtained with this aerosol sampler constructed according to this inventory, although the invention is applicable to achieving any desireable cut point.

The airflow with unremoved particles smaller than 10 microns then enters the lower portion of the middle tube 18 where the trajectory is altered and airflow continues in an upward ascention through the annulus of the upper portion of the middle tube 18. As the airstream exits the upper end 19 of the middle tube 18, an additional turn is made to alter the flow of air into a downward trajectory through the annulus of the outer tube 24. The airflow then continues downwardly through the vacuum tube 48 where the unremoved particles will be deposited on a conventional collection filter substrate (not shown) for subsequent mass analysis.

In ambient aerosol inlet sampler such as that disclosed in this invention with appropriate sized components in the entire inlet structure, including the fractionator 12, the cut point of particulate fractionation can be achieved within 10 percent of the required 10 micron size for the currently recognized standard inhalable particles or TP or any other specific size fraction required. Also, it is important that most if not all of the mass that deposits in the cyclone fractionator is removed by the inner tube and that there are no losses on the air ramp, in the vane structure, or in the middle or outer tubes. When this result is attained, the inner and middle tubes can function as a collective reservoir. Undesirable means build-up on the air ramp 36 or in the vanes 30, could substantially interfere with air flow and the accuracy of the aerosol sample. Undesirable mass build-up on walls of the middle and outer tubes could result in enrichment of various test results if such particles collected in a previous test were dislodged and deposited on the filter substrate during a subsequent test. Therefore, by avoiding undesirable particle build-up in these components, unpredictable maintainance requirements and inaccurate test results can also be avoided.

For purposes of example and not for limitation, the following description illustrates the construction of a 0.589 c.f.m. model of the present invention that has been shown by test results to collect almost exactly the same amount of mass as would be collected in the thoracic region of the respiratory tract of humans. The inner tube 14 is 3.39 inches in length and has an inside diameter of 0.652 inches. The middle tube 18 is 6.4 inches long and has an inside diameter of 1.885 inches. While these dimensions are preferred, quite suitable results have been obtained where the ratio of the inner tube inside diameter to the middle tube inside diameter is in the range of 0.25 to 0.50. Likewise, an acceptable ratio for the inside diameter of the inner tube to its length is in the range of 0.10 to 0.40. The outer tube 24 is 9.092 inches in length and has an inside diameter of 2.43 inches. Each vane 30 is 1.464 inches long, 0.5 inches high, and 0.295 inches at its thickest point. While these dimensions represent the preferred construction of the vanes, it has been found acceptable for the vanes to be formed in such manner that the ratio of the thickest portion of the vane to its length be in a range of 0.10 to 0.30 and the ratio of the height of each vane to its length be in a range of 0.2 to 2.0. The air ramp 36 is approximately 8.64 inches high, the diameter of its upper end 37 is 3.97 inches, the diameter of its narrowest portion at mid-section 38 is 2.5 inches, and the flared lower rim 39 is approximately 6.10 inches in diameter. Again, these dimensions for the ramp are those according to the preferred embodiment of the present invention. It has been found acceptable for the ratio of the ramp's narrowest diameter to the diameter of the ramp's top to be in a range of 0.50 to 0.75. The cover 40 is 8.875 inches in height, and it is approximately 6.1 inches in outside diameter. The inner tube 14 is positioned to extend into the middle tube 18 less than two thirds, and preferably even slightly less than half of the length of the middle tube 18 as shown in FIG. 2. As mentioned above, this model is capable of collecting a sample and fractionating out particles with a $D_{50}$ equal to 10 microns and allowing the remaining particles to flow through and be deposited on the collection substrate filter (not shown) for subsequent mass analysis. The results are independent of wind direction and velocity from 2 to 24 kilometers per hour. These results are almost exactly the same as particles collected by a person's lungs in the TP fraction.

An alternative embodiment 50 is shown in FIGS. 5 and 6, which is effective to obtain accurate sampling results in medium to high volume tests such as in the range of 4 c.f.m. to 40 c.f.m. This alternative embodiment ambient aerosol sampler inlet 50 has a fractionator structure 52 similar to that described in the preferred embodiment above. It includes a first or inner tube 54 positioned partially inside a second or middle tube 58. The lower end 60 of the middle tube 58 is plugged by a plug 61, and the upper end 55 of the inner tube 54 extends upwardly beyond the upper end 59 of middle tube 58. A third or outer tube 64 is positioned concentrically around the middle tube 58. The upper end 65 of outer tube 64 is plugged by vane assembly base 68 a spaced distance above the upper end 59 of middle tube 58. A plurality of vanes 70 are positioned around the center bore 69 in vane assembly base 68, and an aerodynamic ramp 76 is fastened to and extends downwardly from the peripheral surface of the vane assembly base 68. A cylindrical cover 80 is positioned concentrically over the air ramp 76 and is closed on the top over the vanes 70 to define an airflow path from the exterior of the sampler into the vanes 70.

Figure 6:
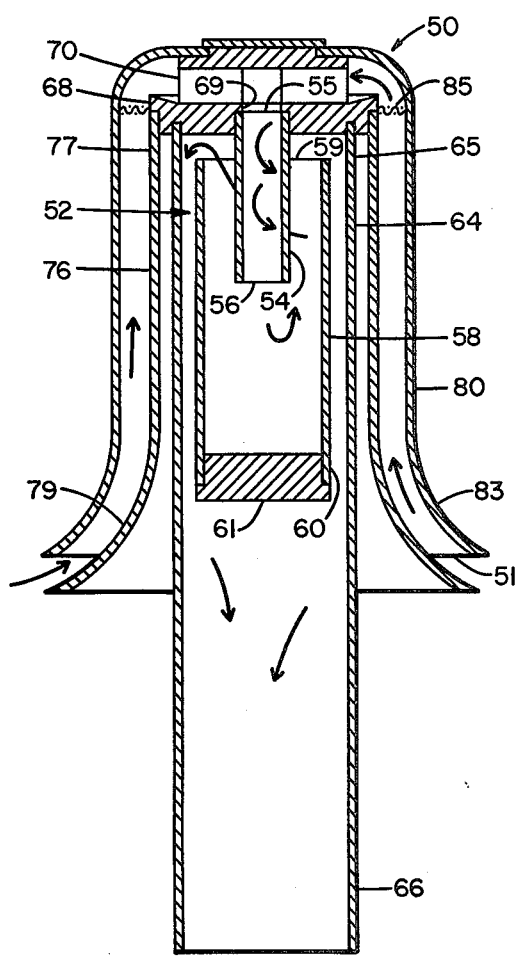
FIG. 6 is a cross-sectional view of the alternate embodiment taken along lines 6—6 of FIG. 5.

In this alternative embodiment, as best shown in FIG. 6, the air ramp 76 is essentially cylindrical in shape with an outwardly flared portion 79 at its lower end. The cover 80 is similarly shaped with an outwardly flared portion 83 at its lower end to define an omni-directional aerodynamic inlet 51 between the respective flared lower ends 79, 83 of the air ramp 76 and cover 80.

This alternative embodiment, of course, operates in essentially the same fashion as the preferred embodiment described above. A conventional vacuum pump and filter collection substrate (not shown) are connected to the lower end 66 of outer 64 to draw air through the fractionator. A sample of ambient aerosol is collected by the omni-directional aerodynamic inlet 51 and is guided over the ramp 76 into the vanes 70. The vanes 70 impart an angular flow to the air as it enters the inner tube 54 in a vortical motion. Most or substantially all of the mass of particles above the desired cut point size, for example 10 microns, is collected in the inner tube 54. The airstream then reverses direction in the middle tube 58 and flows upwardly to the outer tube 64 and then downwardly toward the filter collection substrate and vacuum pump (not shown). A bug screen 85 is positioned in the aerodynamic inlet pathway near the top 77 of the air ramp 76 to prevent flying insects or large debris from entering the smpler.

While the present invention has been described with some degree of particularity, it should be appreciated that the present invention is defined by the following claims contrued in light of the prior art so that modification or changes may be made to the embodiments of the present invention without departing from the inventive concepts comprised herein.

What I claim is:

1. An ambient aerosol sampling device, comprising:
    cyclonic particle fractionating means including an elongated middle tube having a closed bottom and an open top and an elongated inner tube having an inlet and an outlet and having a diameter smaller than said middle tube, said inner tube positioned at least partially inside of said middle tube and extending through said open top with said outlet located interiorly of said middle tube to define an annular outlet opening for said middle tube at the open top thereof, said particle fractionating means for separating solid particles from a stream of air moving through said inner and middle tubes;
    an elongated outer tube positioned concentrically around and extending upwardly above said middle tube, and plug means in the top of said outer tube above said middle tube for sealing the region between the top of said outer tube and the inlet of said inner tube;
    air flow exhaust means in fluid communication with the interior of said outer tube for drawing off a flow of air passing through said inner, middle, and outer tubes; and
    air directing means for introducing a stream of air into said inlet whereby said air flow is caused to undergo vortical motion about the axis of said inner tube, said air flow passing through said air directing means, through said inner tube, through said middle tube and exhausting through said air flow exhaust means.

2. The ambient aerosol sampling device of claim 1, wherein said air directing means includes a plurality of vanes positioned immediately adjacent said inlet in equiangularly spaced apart relation to each other around the inlet of said inner tube of said cyclonic particle fractionating means.

3. The ambient aerosol sampling device of claim 2, wherein each of said vanes has an elongated two dimensional cross section in a plane perpendicular to the longitudinal axis of said inner tube, one side of said cross-section being a straight line beginning at a proximal end adjacent said inlet and extending tangentially outward from said inlet end of said tube to a distal end a spaced distance radially outward from said inlet end of said inner tube and the other side of said cross-section being a smoothly-shaped curve extending from said proximal end of said straight side and diverging away from said straight line to a maximum width and then converging back toward said straight side to intersect said distal end thereof in such a manner that said maximum width is closer to said proximal end than to said distal end.

4. The ambient aerosol sampling device of claim 1, including cylindrical cover means positioned concentrically around said outer tube, said cover means being open at the bottom and having an enclosed top extending over said air directing means for conducting a flow of air from the atmosphere into said air directing means.

5. The ambient aerosol sampling device of claim 4, including aerodynamic flow ramp means positioned inside said cover means and extending downwardly and outwardly from the open bottom thereof in such a manner that the space between the bottom rim of said outer cover means and the bottom rim of said aerodynamic flow ramp means forms an omnidirectional intake for diverting ambient air flow into said ambient aerosol sampling device with the fluid flow of air between said flow ramp and cover means being a substantially laminar flow, said air directing means creating a vortical flow.

6. The ambient aerosol sampling device of claim 5, wherein said aerodynamic flow ramp has a surface of an hourglass-shaped figure of revolution tapered inwardly from its upper end adjacent said air directing means toward its midsection and flared outwardly therefrom in a concave cross-section toward its lower end.

7. The ambient aerosol sampling device of claim 5, wherein the bottom rim of said aerodynamic ramp means is flared outwardly, and the bottom rim of said outer cover means is similarly flared outwardly a spaced distance outward and upward of said flared bottom rim of said aerodynamic ramp means whereby said intake is substantially independent of the radial approach velocity of a stream of air approaching said intake at a radially velocity less than 24 km/hr.

8. The ambient aerosol sampling device of claim 1, wherein the ratio of the inside diameter of said first tube to the inside diameter of said second tube is in the range of 0.25 to 0.50.

9. The ambient aerosol sampling device of claim 8, wherein the ratio of the inside diameter of said first tube to the inside diameter of said second tube is approximately 0.34.

10. An ambient aerosol sampling device, comprising:
    cyclonic particle fractionator means for separating solid particles from an airstream, including an elongated tubular air flow duct having a longitudinal axis and air directing means for imparting a vortical motion to an airstream moving through said duct, said air directing means including a plurality of vanes positioned in angularly spaced apart relation to each other around the inlet end of said duct and adjacent thereto, each of said vanes having a two dimensional cross-section in a plane peripendicular to the longitudinal axis of said duct, including one side of each vane in cross-section being straight and another side of each vane in cross-section being smoothly curved and extending from an intersection with one end of said straight side, diverging away therefrom, and then converging back toward the straight side and intersecting with the other end of said straight side, each of said vanes being oriented with its straight side at an acute angle with the radius of the duct; and intake means for directing a laminar stream of air into said vanes and into said duct, said flow being transformed into a vortical flow by said vanes.

11. The ambient aerosol sampling device of claim 10, wherein the convergence of the curved side of each of said vanes toward said other end of said straight side is at a smaller angle than the divergence of the curved side from said one end such that said straight and curved sides define a thickest portion of said vane closer to said one end of said vane adjacent said duct than to said other end thereof.

12. The ambient aerosol sampling device of claim 11, wherein the ratio of the thickest portion of said vane to the length of said straight side thereof is in the range of 0.10 to 0.30.

13. The ambient aerosol sampling device of claim 11, wherein the ratio of height to length of said vane is in the range of 0.2 to 2.0.

14. An ambient aerosol sampling device for separating from an ambient air stream the particles having a size greater than 10 microns, comprising:

an elongated first tube positioned partially inside a larger diameter elongated second tube having a closed bottom end, one end of said first tube forming an air inlet and protruding upwardly beyond the upper end of said second tube and the other end of said first tube extending downwardly into the interior of said second tube a distance less than two-thirds the length of said second tube;

air flow exhaust means at said upper end of said second tube for drawing off a flow of air through said first and second tubes;

a generally cylindrical cap having a top, an open bottom and a surrounding sidewall and having an aerodynamic flow ramp defined by a figure of revolution flared outwardly at its bottom and oriented concentrically in said cover cap, said first and second tubes being positioned axially within said figure of revolution, said cap having an annular air intake opening between said open bottom and said flow ramp whereby said air intake is omnidirectional in radial directions, said sidewall and said flow ramp configured to cause laminar flow of air flowing therebetween from said air intake to a location adjacent said air inlet; and vortical air directing means adjacent said air inlet for imparting a vortical motion to said laminar flow of air at said location at said air inlet and causing said vortical motion through said first tube.

15. The ambient aerosol sampling device of claim 14, wherein said vortical air directing means includes a plurality of vanes positioned equiangularly around said air inlet and having a height at least as great as the distance between said air inlet and said top, each vane having a first straight surface oriented generally perpendicularly to said top and extending substantially tangentially to said air inlet and a second curved surface also oriented generally perpendicular to said top and extending outwardly in a smooth curve from an intersection with said straight surface adjacent said inlet to diverge away from, and then converge back toward, said straight surface.

16. The ambient aerosol sampling device of claim 14, wherein the ratio of the inside diameter to the length of said first tube is in the range of 0.10 to 0.40.

17. An ambient aerosol sampling device, comprising:
cyclonic particle fractionator means for separating solid particles from an airstream and having an air inlet and an air outlet; and an omnidirectional air intake assembly operative to direct a flow of air into said cyclonic particle fractionator means and including a generally cylindrical cover member having a top plate extending across said air inlet in spaced-relation thereto and having a surrounding sidewall with a lower edge opposite said top plate, said intake assembly further including a tubular aerodynamic flow deflector having an hourglass-shaped figure of revolution flared outwardly from its midsection to both its ends in a concave cross-section to define an air intake between said lower edge and said deflector, said deflector oriented coaxially with said cover member and operative in conjunction with said sidewall to cause a laminar flow of air from said intake to said air inlet.

18. The ambient aerosol sampling device of claim 17, wherein the ratio of the diameter of the narrowest portion of said aerodynamic flow deflector to the diameter of the top thereof is in the range of 0.50 to 0.75.

* * * * *

UNITED STATES PATENT AND TRADEMARK OFFICE
CERTIFICATE OF CORRECTION

PATENT NO. : 4,461,183
DATED : July 24, 1984
INVENTOR(S) : James B. Wedding

It is certified that error appears in the above-identified patent and that said Letters Patent is hereby corrected as shown below:

Background of the Invention

Column 1, line 9, after "air." insert the following new paragraph:
-- The invention described herein (or "in this patent") was made in the course of work under U.S. Environmental Protection Agency Cooperation Agreement No. CR808011. The Government of the United States has certain rights in this invention.--
Column 1, line 19, delete "nular" and substitute --nual--.
Column 1, line 26, delete "on" and substitute --in--.
Column 1, line 29, delete "TPC" and substitute --TP--.
Column 1, line 38, delete "particu-" and substitute --particle--.
Column 1, line 39, delete "late".
Column 1, line 47, delete "and".

Summary of the Invention

Column 1, line 67, delete "in" and substitute --to--.
Column 2, line 8, after "substrate" insert --a--.

Detailed Description of the Preferred Embodiment

Column 4, line 4, delete "structure" and substitute --structural--.
Column 4, line 36, delete "side".
Column 4, line 50, delete "downwardly" and substitute --inwardly--.

Column 5, line 51, after "In" insert --an--.
Column 5, line 64, delete "means" and substitute --mass--.

Column 7, line 34, delete "smpler" and substitute --sampler--.

UNITED STATES PATENT AND TRADEMARK OFFICE
CERTIFICATE OF CORRECTION

PATENT NO. : 4,461,183
DATED : July 24, 1984
INVENTOR(S) : James B. Wedding

It is certified that error appears in the above-identified patent and that said Letters Patent is hereby corrected as shown below:

Column 8, Claim 3, line 17, after "said", second occurrence, insert -- inner --.

Signed and Sealed this

Seventh Day of May 1985

[SEAL]

Attest:

DONALD J. QUIGG

Attesting Officer     Acting Commissioner of Patents and Trademarks